US012622806B2

(12) United States Patent
Sundar et al.

(10) Patent No.: US 12,622,806 B2
(45) Date of Patent: May 12, 2026

(54) WEARABLE LIMB WRAPS FOR TEMPERATURE-CONTROLLED THERAPY

(71) Applicants: NATIONAL UNIVERSITY HOSPITAL (SINGAPORE) PTE LTD, Singapore (SG); NATIONAL UNIVERSITY OF SINGAPORE, Singapore (SG); PAXMAN COOLERS LTD, Huddersfield (GB)

(72) Inventors: Raghav Sundar, Singapore (SG); Aishwarya Bandla, Singapore (SG); Jonathan Rex Binder, Huddersfield (GB); Patrick Burke, Sheffield (GB); Ertu Unver, Huddersfield (GB)

( * ) Notice: Subject to any disclaimer, the term of this patent is extended or adjusted under 35 U.S.C. 154(b) by 532 days.

(21) Appl. No.: 18/251,884

(22) PCT Filed: Nov. 5, 2021

(86) PCT No.: PCT/SG2021/050677
§ 371 (c)(1),
(2) Date: May 5, 2023

(87) PCT Pub. No.: WO2022/098309
PCT Pub. Date: May 12, 2022

(65) Prior Publication Data
US 2023/0414445 A1 Dec. 28, 2023

(30) Foreign Application Priority Data
Nov. 5, 2020 (SG) ............................ 10202011037W

(51) Int. Cl.
*A61F 7/02* (2006.01)
*A61F 7/10* (2006.01)
(Continued)

(52) U.S. Cl.
CPC .................. *A61F 7/02* (2013.01); *A61F 7/10* (2013.01); *A61H 9/0092* (2013.01);
(Continued)

(58) Field of Classification Search
CPC ...... A61F 7/02; A61F 7/10; A61F 2007/0034; A61F 2007/0036; A61F 2007/0056;
(Continued)

(56) References Cited

U.S. PATENT DOCUMENTS 10,456,320 B2 * 10/2019 Lowe ..................... A61H 9/005
2013/0253383 A1 9/2013 Maxon-Maldonado
(Continued)

FOREIGN PATENT DOCUMENTS

WO 2014158461 A1 10/2014
WO 2018052676 A1 3/2018
WO WO-2020223721 A1 * 11/2020 ........... A61H 9/0078

*Primary Examiner* — Shaun R Hurley
(74) *Attorney, Agent, or Firm* — SOROKER AGMON NORDMAN

(57) ABSTRACT

A compression wrap and method for temperature-controlled application of pressure on an arm of a subject, comprising a fluid bladder comprising a first element comprising two or more first flaps; a second element comprising one or more digital flaps; and a third element comprising two or more second flaps, wherein the first element and the third element are connected along a first edge and the second element is connected to the first element and the third element along a second edge.

18 Claims, 7 Drawing Sheets

(51) Int. Cl.
  *A61H 9/00*          (2006.01)
  *A61F 7/00*          (2006.01)
(52) U.S. Cl.
  CPC ................. *A61F 2007/0036* (2013.01); *A61F*
      *2007/0056* (2013.01); *A61F 2007/0091*
    (2013.01); *A61F 2007/0225* (2013.01); *A61F*
      *2007/0249* (2013.01); *A61H 2201/0214*
    (2013.01); *A61H 2201/0242* (2013.01); *A61H*
      *2201/1635* (2013.01); *A61H 2201/165*
      (2013.01); *A61H 2205/065* (2013.01)
(58) Field of Classification Search
  CPC ...... A61F 2007/0091; A61F 2007/0225; A61F
      2007/0249; A61H 9/0092; A61H
      2201/0214; A61H 2201/0242; A61H
      2201/1635; A61H 2201/165
  See application file for complete search history.

(56)                References Cited

U.S. PATENT DOCUMENTS

2014/0142473  A1*   5/2014  Lowe ................... A61H 9/0092
                                                    601/84
2014/0276253  A1*   9/2014  Varga ................... A61H 9/0078
                                                    601/15
2014/0276254  A1*   9/2014  Varga ................... A61H 9/0007
                                                    601/15
2014/0277301  A1*   9/2014  Varga ........................ A61F 7/02
                                                    607/104
2015/0150717  A1    6/2015  Lowe et al.
2018/0161200  A1    6/2018  Wilford

* cited by examiner

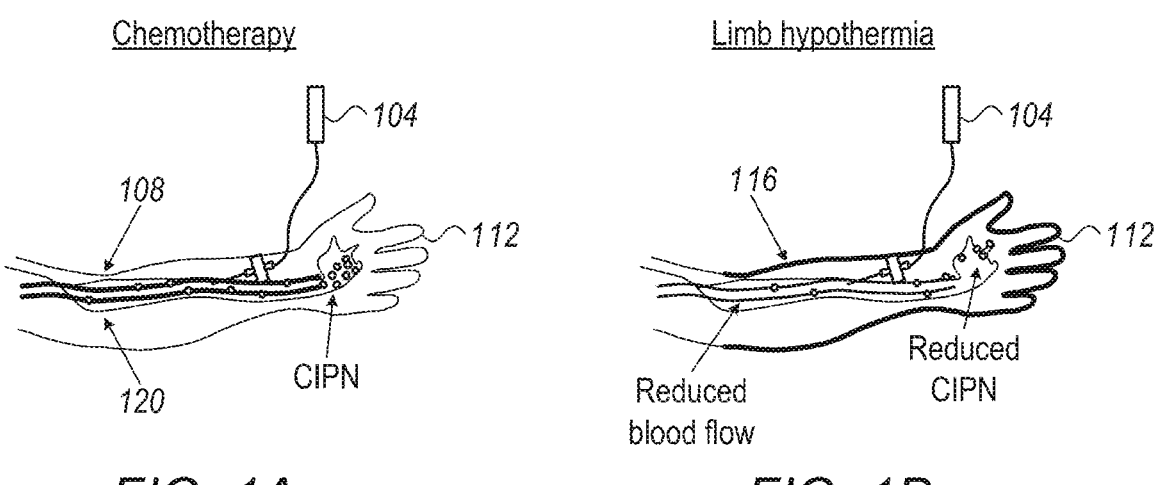
Chemotherapy
Limb hypothermia
*FIG. 1A*          *FIG. 1B*
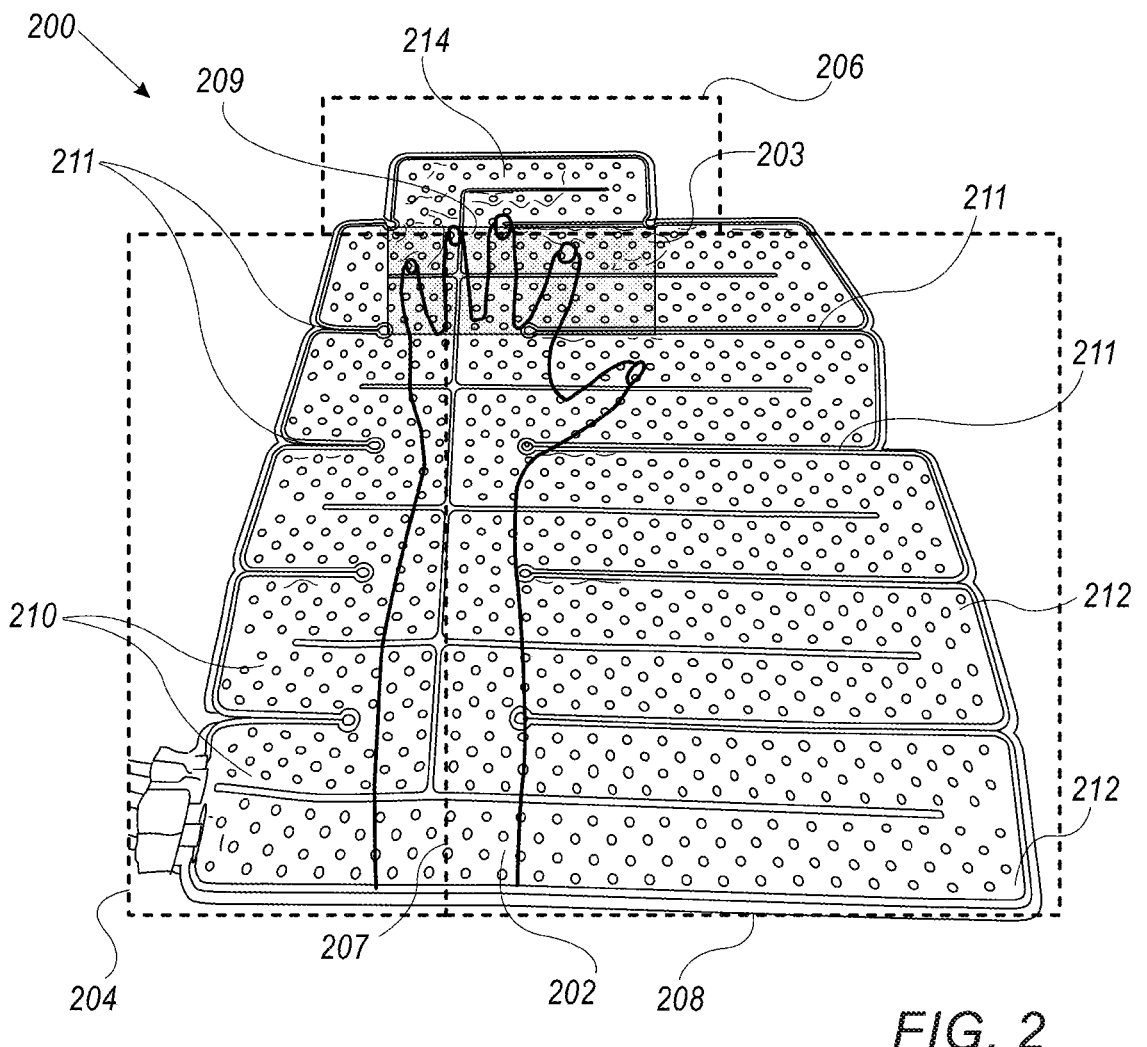
*FIG. 2*

404
402
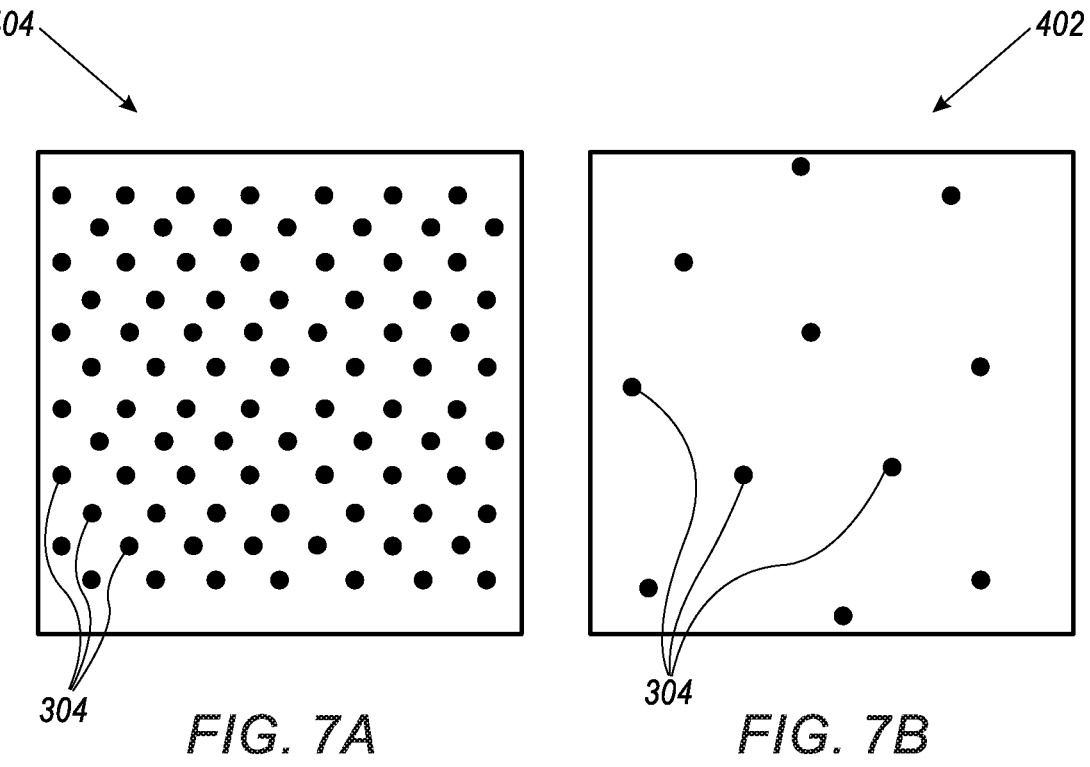
304
*FIG. 7A*
304
*FIG. 7B*
202
210
802
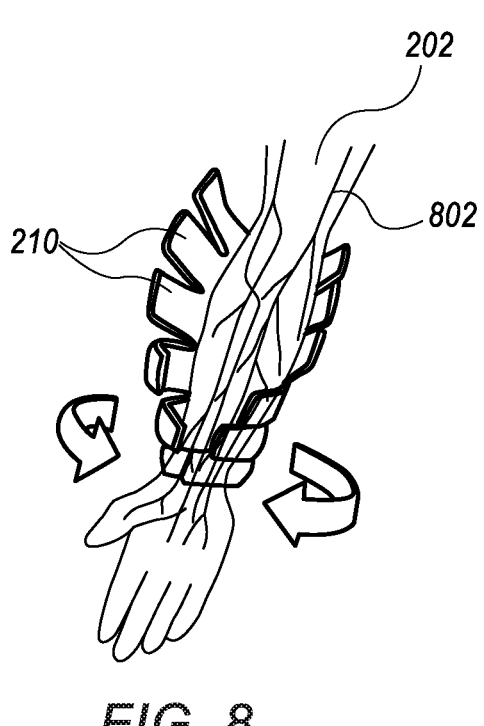
*FIG. 8*

WEARABLE LIMB WRAPS FOR TEMPERATURE-CONTROLLED THERAPY

TECHNICAL FIELD

The present disclosure relates to the field of supportive care. In particular, the present disclosure relates to a compression wrap for providing heating or cooling to a limb.

BACKGROUND

Compression is the squeezing of a body part in a device, wrap or sleeve to apply pressure to the body part. Heating or cooling may sometimes be carried out simultaneously by circulating a temperature-controlled fluid within a bladder contained within the device, wrap or sleeve. For example, cooling may be simultaneously carried out to effect cryocompression, which is to simultaneously apply pressure to the body part while reducing the temperature of the body part. Cryocompression has uses in various fields, including the cosmetic and medical fields. For example, cryocompression may be used to prevent and/or treat chemotherapy-induced peripheral neuropathy (CIPN). CIPN is a severe dose-limiting side-effect of several commonly used chemotherapeutic agents used in chemotherapy for cancer treatment. CIPN causes progressive and often irreversible pain/sensitivity in hands and feet and affects cancer survival rates as it may cause delay and discontinuation of chemotherapy. Overall, CIPN affects a significant number of cancer patients annually worldwide and contributes to long-term morbidity for cancer patients. CIPN also significantly increases economic burden, with healthcare costs estimated to be US$17,000 more in cancer patients with CIPN than those without CIPN. CIPN also causes patient work-loss, with a productivity loss of some 50 days with usual care.

There is an unmet and increasing clinical need for systems, devices, and methods to prevent/treat CIPN in cancer patients receiving chemotherapy treatment. Available treatment methods for CIPN are limited to alleviating symptoms such as paraesthesia, dysesthesia, and pain. Although several methods involving pharmacological agents have been developed, such as supplementation with Vitamin E or omega-3, none have proven effective in large-scale clinical trials.

Limb cooling during chemotherapy treatment has demonstrated a neuroprotective effect by preventing/reducing CIPN severity. Studies have shown that the extent of neuroprotection is dependent on the efficiency of limb hypothermia, i.e., the degree of cooling achieved.

Reference is made to FIGS. 1A and 1B, which illustrate a subject receiving chemotherapy treatment with and without limb hypothermia respectively. A subject may receive chemotherapy through the introduction of neurotoxic chemotherapeutics 104, like Paclitaxel, into the arm. Systematic cancer treatment with neurotoxic chemotherapeutics has been shown to cause inflammation and nerve damage in, for example, the ulnar nerve 108. This nerve damage manifests as numbness and tingling sensation in the limbs such as hand 112 and is known as CIPN. Limb hypothermia 116 prevents CIPN by causing vasoconstriction of the cooled regions such as ulnar vein 120 and reduces exposure of the region to the chemotherapeutics by reducing blood flow to the region. Limb hypothermia also reduces inflammation in the subject.

Among various cryotherapy modalities available for use, ice packs and commercially available gel packs are the most frequently used modalities. Due to risk of frost bite and subject intolerance of the temperature, studies have recommended intermittent cooling schedules of 30 minutes cooling coupled with 30 minutes of rewarming. However, such an intermittent routine might not be efficacious, or even worse, be counter-productive due to rebound blood flow. Furthermore, ice packs can cause extensive variations in temperature due to their phase change during melting.

Gloves were previously used frozen to administer limb cryotherapy to cancer patients. However, these gloves were not operator-friendly, delivered unstable cooling and caused subject discomfort which limited the period of application of cryotherapy. These gloves were eventually withdrawn from the market due to incidences of frostbite.

Existing apparatuses utilising continuous-controlled coolant flow use dated vapour compression technology, which is heavy and cumbersome, thus restricting subject-mobility and the environment of use, and consequently its range of applications. Although there are other methods for cooling, these have problems or restrictions associated. For example, cooling using the Peltier effect cannot achieve the required cooling rates whilst remaining portable. On the other hand, cooling using the Magnetocaloric effect is still at the research phase and is not yet market accessible.

Other existing cooling solutions are either bulky, manpower intensive, energy inefficient, and do not cater for use in preventing CIPN in cancer patients. In particular, these cooling technologies do not have cooling accessories which are catered for use during chemotherapy administration, which requires the limb of the subject to be cannulated and monitored.

There is therefore a need for accessories specifically designed for cancer patients undergoing chemotherapy and to make possible concomitant administration of cryotherapy feasible, optimal and efficacious.

SUMMARY

One general aspect includes a compression wrap for temperature-controlled application of pressure on an arm of a subject. The compression also includes a fluid bladder may include: a first element may include two or more first flaps; a second element may include one or more digital flaps; and a third element may include two or more second flaps, where the first element and the third element are connected along a first edge and the second element is connected to the first element and the third element along a second edge.

Implementations may include one or more of the following features. The compression wrap where the first element of the fluid bladder is configured to cover at least a first half of a circumference of the arm of a subject and the third element of the fluid bladder is configured to cover at least a second half of the circumference of the arm of a subject. Each of the two or more second flaps corresponds to one of the two or more first flaps. Each of the two or more second flaps is removably attached to a corresponding first flap. The two or more first flaps and the two or more second flaps extend perpendicularly from the first edge. The two or more first flaps are separated from each other with slits terminating within the first element. The two or more second flaps are separated from each other with slits terminating within the third element. The fluid bladder may include an air cavity and a liquid cavity. The air cavity may include between 0.25 and 2 attachment points per square inch. The air cavity may include attachment points with a pitch ratio height of between 15 and 50 mm and a pitch ratio width of between 20 to 100 mm. The liquid cavity may include a liquid inlet and a liquid outlet, the liquid cavity may include a passageway that runs through the liquid cavity from the liquid inlet to the liquid outlet. The passageway runs along a perimeter of each of the two or more first flaps, the one or more digital flaps, and two or more second flaps. The liquid inlet is positioned on a first flap or second flap distal from the second element. The liquid cavity may include between 3 and 8 attachment points per square inch. The liquid cavity may include attachment points with a pitch ratio height of between 5 and 40 mm and a pitch ratio width of between 5 and 40 mm. The liquid cavity may include three or more liquid pockets. The compression wrap may include a fabric layer positioned against the liquid cavity and an insulating layer positioned against the air cavity.

One general aspect includes a method of applying temperature-controlled pressure to an arm of a subject. The method of applying temperature-controlled pressure also includes providing a compression wrap, the compression wrap may include: a fluid bladder may include: a first element may include two or more first flaps; a second element may include one or more digital flaps; and a third element may include two or more second flaps, where the first element and the third element are connected along a first edge and the second element is connected to the first element and third element along a second edge. The pressure also includes securing the compression wrap on the arm by attaching each of the two or more second flaps to a corresponding first flap. The pressure also includes injecting air and coolant into the fluid bladder.

Implementations may include one or more of the following features. The method where coolant is injected into a liquid cavity of the fluid bladder, the liquid cavity positioned against the subject. Air is injected into an air cavity of the fluid bladder, the air cavity positioned above the liquid cavity. Air is injected into and released from the air cavity intermittently to provide cyclical pressure on the subject. The method may include detaching and reattaching one of the two or more second flaps from the corresponding first flap to monitor the subject.

BRIEF DESCRIPTION OF THE DRAWINGS

Features, aspects, and advantages of the present disclosure will become better understood with regard to the following description and accompanying drawings in which:

FIGS. 1A and 1B illustrate a subject receiving chemotherapy treatment with and without limb hypothermia respectively;

FIG. 2 is a schematic illustration of a fluid bladder, in accordance with embodiments of the present disclosure;

FIG. 7A is a schematic illustration of a density of attachment points on a liquid cavity, in accordance with embodiments of the present disclosure;

FIG. 7B is a schematic illustration of a density of attachment points on an air cavity, in accordance with embodiments of the present disclosure;

FIG. 8 is a schematic illustration of first flaps and second flaps of fluid bladder 200 wrapped around a forearm of a subject, in accordance with embodiments of the present disclosure;

Figure 3:
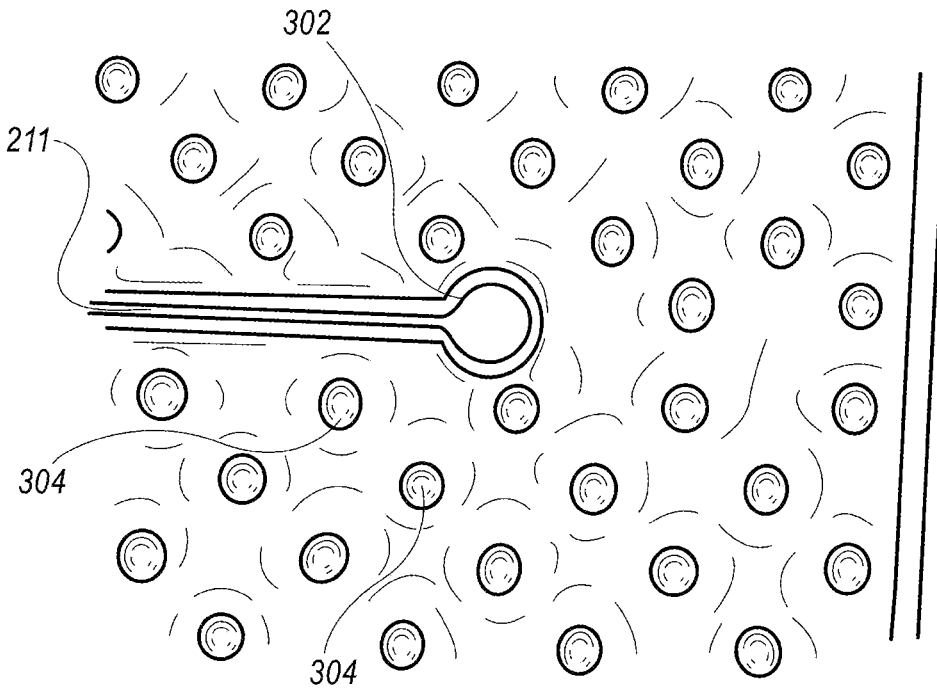
FIG. 3 is a schematic illustration an end of a slit of a fluid bladder, in accordance with embodiments of the present disclosure.

Identical or duplicate or equivalent or similar structures, elements, or parts that appear in one or more drawings are generally labelled with the same reference numeral, optionally with an additional letter or letters to distinguish between similar entities or variants of entities and may not be repeatedly labelled and/or described. References to previously presented elements are implied without necessarily further citing the drawing or description in which they appear.

DETAILED DESCRIPTION

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

FIG. 2 is a schematic illustration of a fluid bladder 200 in accordance with embodiments of the present disclosure. Fluid bladder 200 may be flexible and may be made of plastic or any non-porous material. In some embodiments, fluid bladder 200 may be designed to be secured around an arm of a subject 202. In some embodiments, fluid bladder 200 may be designed to be secured around a lower arm of subject 202, including a forearm, palm, and fingers. In some embodiments, fluid bladder 200 may comprise a first element 204 for covering at least a first half of a circumference of the arm, a second element 206 for covering the digits or fingers and a third element 208 for covering at least a second half of the circumference of the arm, each of the elements 204, 206 and 208 joined to the other two elements. In some embodiments, first element 204 and second element 206 may have the same length and may be connected to each other lengthwise over any distance along a first edge 207. In some embodiments, first edge 207 may run an entire length of the first element 204 and second element 206. In some embodiments, first edge 207 may run over a portion of the lengths of the first element 204 and second element 206. In some embodiments, third element 208 may be connected lengthwise to the widths of the first element 204 and second element 206 along a second edge 209. First element 204, second element 206, and third element 208 may be joined or connected using any method, including mechanical fastening, adhesive, solvent bonding, and welding.

According to some embodiments of the present disclosure, first element 204 may comprise two or more first flaps 210 arranged parallel along first edge 207, the two or more first flaps 210 extending perpendicularly from first edge 207. In some embodiments, first flaps 210 may be separated from each other with slits 211 terminating within first element 204, such that each first flap 210 may be manipulated independently from other first flaps 210. In some embodiments, slits 211 may define a gap or distance between adjacent first flaps 210.

According to some embodiments of the present disclosure, third element 208 may comprise two or more second flaps 212 arranged parallel along first edge 207, the two or more second flaps 212 extending perpendicularly from first edge 207. In some embodiments, second flaps 212 may be separated from each other with slits 211 terminating within third element 208, such that each second flap 212 may be manipulated independently from other second flaps 212. In some embodiments, slits 211 may define a gap or distance between adjacent second flaps 212.

According to some embodiments of the present disclosure, the number and positions of second flaps 212 may correspond to the number and positions of first flaps 210. In some embodiments, first flaps 210 and second flaps 212 may be positioned, arranged, and dimensioned such that each first flap 210 wraps around at least a first half of the circumference of an arm of subject 202 and a corresponding second flap 212 wraps around at least a second half of the circumference of the arm of subject 202 and overlaps the first flap 210 to be removably secured to the first flap 210. In some embodiments, each second flap 212 may be removably attached or secured to a corresponding first flap 210 through any securing mechanism, including using a sleeve 406 with hook and loop material, also known as Velcro. Second flaps 212 and first flaps 210 may have flat or slanted ends. The person skilled in the art will appreciate that the ends of second flaps 212 and first flaps 210 may be flat or slanted to cater for the tapering shape of the arm of subject 202 and to ensure a snug fit. Preferably, there are five or more first flaps 210 and five or more second flaps 212. In some embodiments, there may be three first flaps 210 and three second flaps 212 spanning a forearm region of a subject 202. In some embodiments, there may be two first flaps 210 and two second flaps 212 spanning a palm and finger region of a subject 202. In some embodiments, first flaps 210 may be of equal or varying lengths. In some embodiments, second flaps 212 may be of equal or varying lengths. Preferably, the lengths of the first flaps 210 and second flaps 212 correspond with the region of the arm they are designed to wrap around. Preferably, the ratio of the lengths of second flaps 212 to first flaps 210 may be between 3:1 and 2:1. Preferably, first flaps 210 designed to wrap around the forearm region of a subject 202 may have a length of between 80 and 130 mm, and ideally between 110 and 125 mm, while second flaps 212 designed to wrap around the forearm may have a length of between 200 and 330 mm, and ideally between 235 and 260 mm. Preferably, first flaps 210 may be designed to wrap around the palm and finger region of a subject 202 and may have a length of between 70 and 110 mm, and ideally between 80 and 100 mm, while second flaps 212 may be designed to wrap the palm and finger region of a subject 202 and may have a length of between 150 and 280 mm, and ideally between 170 and 220 mm. Persons skilled in the art will appreciate that the first flaps 210 and second flaps 212 may be of any length so long as the first flap 210 and second flap 212 are able to fully wrap around the circumference of the arm of the subject 202 when connected to each other.

According to some embodiments of the present disclosure, second element 206 may comprise one or more digital flaps 214. In some embodiments, the one or more digital flaps 214 may be configured to fold back over and cover digits or fingers of the subject 202 as illustrated as shaded region 203, and subsequently covered by the first element 204 and third element 208 when fluid bladder 200 is in use. In other embodiments, the first element 204 and third element 208 may first be secured around the arm of the patient and the one or more digital flaps 214 may then fold back over the digits or fingers of the subject 202 and secured to the first element 204 or third element 208. In some embodiments, digital flap 214 may have a length of between 90 and 200 mm, and preferably 110 mm, and a width of between 60 and 120 mm, and preferably 90 mm. In some embodiments, there may be two digital flaps 214, each of the digital flaps 214 connected to either first element 204 or third element 208. In some embodiments, the one or more digital flaps 214 may further comprise skin temperature sensors (not shown), the skin temperature sensors positioned such that they come into contact with the subject 202 when in use. Skin temperature sensors may also be positioned anywhere on fluid bladder 200 as long as they come into contact with the skin of the subject 202 when fluid bladder 200 is in use.

Reference is made to FIG. 3, which is a schematic illustration of an end of a slit 211 of fluid bladder 200, in accordance with embodiments of the present disclosure. In some embodiments, ends of the slits 211 separating first flaps 210, digital flap 214 and second flaps 212 may comprise press crimp welds 302. In some embodiments, the press crimp welds 302 may be circular. Press crimp welds 302 located at the ends of slits 211 confer advantages like expansion for torsion forces applied when the fluid bladder 200 is wrapped around the arm of a subject 202, bend allowance to help alleviate certain pressures generated when the flat fluid bladder 200 is filled and moulded into a 3D object wrapped around the arm of a subject 202, as well as strengthening of the ends of the slits 211 to prevent tearing and other damage of the flaps.

According to some embodiments of the present disclosure, fluid bladder 200 may comprise numerous attachment points 304 along its surface, the attachment points 304 joining the layers or walls comprising the fluid bladder 200. In some embodiments, the attachment points 304 may be welded dots, the welded dots being circular in shape, although other shapes may also be employed. In some embodiments, attachment points 304 may be formed by spot welding or thermal melting of the layers or walls comprising the fluid bladder 200. The numerous attachment points 304 serve to prevent ballooning of the fluid bladder 200 under pressurised liquid and/or air which could otherwise lead to bursting.

Figure 4:
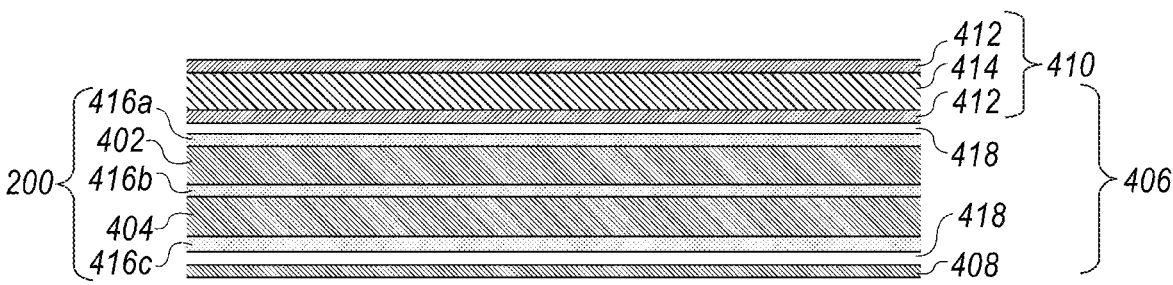
FIG. 4 is a schematic illustration of a cross-section of a fluid bladder between a fabric layer and an insulating layer, in accordance with embodiments of the present disclosure.

Reference is made to FIG. 4, which is a schematic illustration of a cross-section of fluid bladder 200 between a fabric layer 408 and an insulating layer 410, in accordance with embodiments of the present disclosure. Preferably, fabric layer 408 and insulating layer 410 may be in contact with fluid bladder 200, but optionally there may be gaps 418 between fabric layer 408 and fluid bladder 200, and between insulating layer 410 and fluid bladder 200. In some embodiments, fluid bladder 200 may comprise three walls 416a, 416b and 416c forming two cavities with wall 416b as a common wall. In some embodiments, walls 416 may be plastic sheets or layers. In some embodiments, the two cavities may be an air cavity 402 formed by walls 416a and 416b, and a liquid cavity 404 formed by walls 416b and 416c, such that the air cavity 402 and liquid cavity 404 share wall 416b as a common wall. In some embodiments, liquid cavity 404 may receive coolant while air cavity 402 may receive air. In some embodiments, the coolant may be an organic salt-based freeze depressant with a pH buffer. In some embodiments, the coolant may be any desired temperature above or below a body temperature of the subject. In some embodiments, where fluid bladder 200 is used to cool a limb of a subject, the coolant may be of any temperature between 6 and 24° C. Preferably, the coolant will have a density of 1.0 to 1.5 kg*m² at 20° C. to allow smooth flow in and out of liquid cavity 404 during application of the fluid bladder 200. In some embodiments, the coolant may comprise potassium formate (CAS No: 590-29-4) (20-40%), dipotassium phosphate (CAS No: 7758-11-4) (0.5-5%) and deionised water (CAS No: 7732-18-5) (50-70%). In some embodiments, when fluid bladder 200 is secured around the arm of subject 202, liquid cavity 404 may be positioned proximate to the skin of the subject 202, while air cavity 402 may be positioned above liquid cavity 404 such that when air is pumped into air cavity 402, air cavity 402 expands and compresses liquid cavity 404 inwards onto the skin of the subject 202. This creates pressure on the arm of the subject 202, which has been shown to increase a subject's tolerance to low temperatures such that the subject is able to tolerate lower temperatures when compression or pressure is applied concurrently while cooling.

According to some embodiments of the present disclosure, fluid bladder 200 may be inserted into a sleeve 406 comprising two layers: fabric layer 408 and insulating layer 410. In other embodiments, the fluid bladder 200 may be fixed to fabric layer 408 and insulating layer 410. In some embodiments, fabric layer 408 may be positioned proximate to liquid cavity 404 and may be made of any fabric that is biocompatible as it comes into contact with the skin of a subject 202. In some embodiments, insulating layer 410 may be positioned proximate to air cavity 402 and may comprise any insulating material. Preferably, insulating layer 410 comprises neoprene 414 sandwiched between two layers of lining 412.

Figures 5A, 5B:
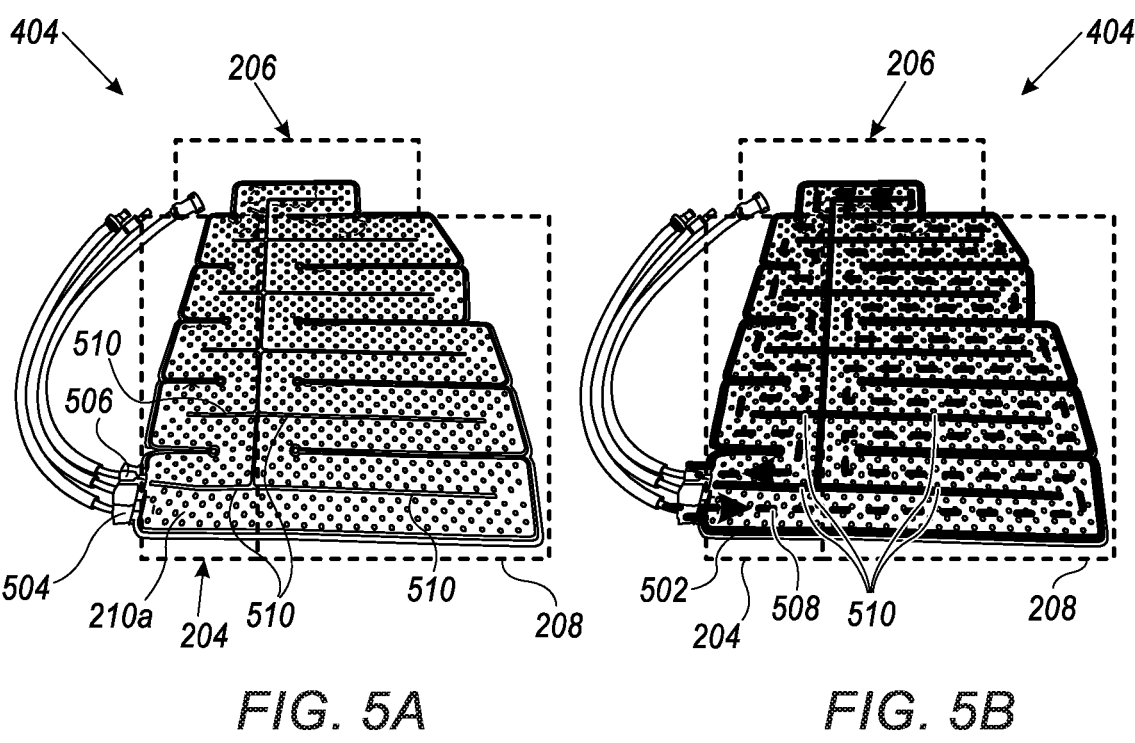
FIG. 5A is a schematic illustration of a liquid cavity of a fluid bladder, in accordance with embodiments of the present disclosure.
FIG. 5B is a schematic illustration of passageway walls of a liquid cavity of a fluid bladder and direction of liquid flow within the liquid cavity, in accordance with embodiments of the present disclosure.

Reference is made to FIG. 5A, which is a schematic illustration of liquid cavity 404 of fluid bladder 200 and FIG. 5B, which is a schematic illustration of passageway walls 502 of liquid cavity 404 of fluid bladder 200 and the direction of liquid flow 508 within the liquid cavity 404, in accordance with embodiments of the present disclosure. According to some embodiments, the liquid cavity 404 of fluid bladder 200 may comprise a single passageway 502 that runs through the liquid cavity 404 (see FIG. 5B). The passageway 502 ensures a constant flow of coolant during operation to maintain a constant heat exchange.

According to some embodiments of the present disclosure, liquid cavity 404 of fluid bladder 200 may comprise a liquid inlet 504 to receive coolant and a liquid outlet 506 to output coolant. The liquid inlet 504 defines the beginning of passageway 502, while the liquid outlet 506 defines the end of passageway 502 such that coolant received at liquid inlet 504 flows through passageway 502 within liquid cavity 404 of the fluid bladder 200 and exits liquid cavity 404 at liquid outlet 506. Preferably, coolant is introduced into liquid inlet 504 at a flow rate of between 25 and 45 ml/sec, and ideally between 35 and 40 ml/sec. In some embodiments, first element 204, second element 206 and third element 208 may be fluidly connected to each other and may each define a section of passageway 502. Liquid inlet 504 and liquid outlet 506 may be located anywhere along liquid cavity 404. In some embodiments, liquid inlet 504 and liquid outlet 506 may be located at a first flap 210 or second flap 212 distal from second element 206 to be wrapped around the region of the forearm proximate to the elbow of the subject 202. In some embodiments, liquid inlet 504 may be located at a first flap 210 or second flap 212 to be wrapped around the region of the forearm proximate to the elbow of the subject 202 and liquid outlet 212 may be located on any first flap 210 or second flap 212. Preferably, the liquid inlet 504 and liquid outlet 506 are located at a first flap 210a to be wrapped around the region of the forearm proximate to the elbow of the subject 202. In some embodiments, passageway 502 may run from the liquid inlet 504 on first flap 210a of the first element 204 through each of the second flaps 212 of the third element 208, the digital flap 214 of the second element 206 and each of the first flaps 210 of first element 204 before exiting through the liquid outlet 506 on first flap 210a of the first element 204. Preferably, the walls of passageway 502 include press crimp welds 302 where single passageway 502 passes from a preceding flap to a subsequent flap. Preferably, there are attachment points 304 present throughout the cavity walls of single passageway 502 to prevent ballooning of liquid cavity 404 and to generate turbulence which is proven to improve liquid flow rates. An example of a direction of flow of the coolant through passageway 502 is indicated by arrow 508 in FIG. 5B, although other directions of flow may also be possible. Preferably, when the fluid bladder 200 is wrapped around the arm of subject 202, the coolant flow 508 within passageway 502 moves from a region of the forearm closest to the elbow, down the subject's arm to the fingertips and then back up the forearm of the subject 202. This design ensures that cooling is graduated from a highest point of the arm where there is more surface area and thus has more opportunity to extract heat. As the coolant picks up heat whilst moving towards the hand of the subject, much heat has been removed and the coolant is slightly warmer when it reaches the palm and fingertips of the subject. Since subjects may face cold intolerance in the fingers first, the fluid bladder 200 may increase a subject's tolerability and consequently, duration of limb cooling by not exposing the extremities to the lowest temperatures.

According to some embodiments of the present disclosure, passageway 502 within the liquid cavity 404 may have a constant and parametric width and rounded corners to ensure optimal flow rates of coolant within the liquid cavity 404 without bottlenecking or chopping the coolant in corners. In some embodiments, passageway 502 may run along a perimeter of each of the first flaps 210, digital flap 214 and second flaps 212. Preferably, there is a dividing wall 510 within each first flap 210, digital flap 214 and second flap 212 to maximise the width of the passageway 502 (see FIG. 5A).

Figures 6A, 6B:
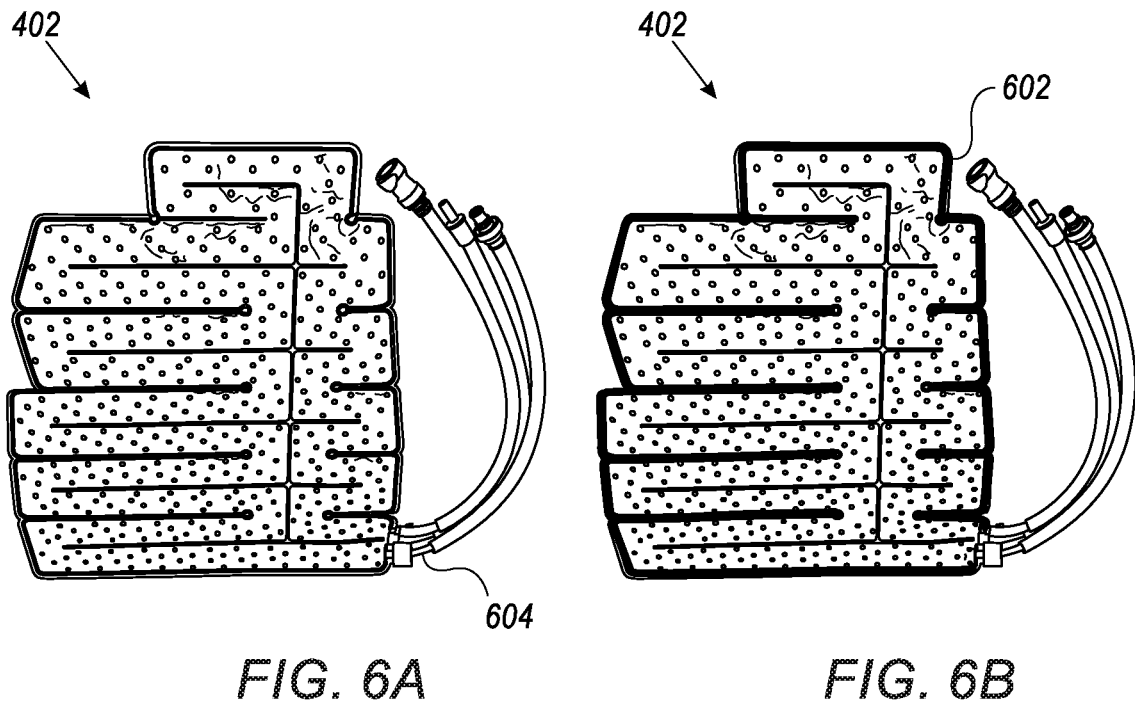
FIG. 6A is a schematic illustration of an air cavity of a fluid bladder, in accordance with embodiments of the present disclosure.
FIG. 6B is a schematic illustration of cavity walls of an air cavity of a fluid bladder, in accordance with embodiments of the present disclosure.

Reference is made to FIG. 6A which is a schematic illustration of the air cavity 402 of a fluid bladder 200, and FIG. 6B which is a schematic illustration of air cavity walls 602 of the air cavity 402 of the fluid bladder 200, in accordance with embodiments of the present disclosure. In some embodiments, air cavity 402 may be single cavity, with the cavity walls 602 along the perimeter of the fluid bladder 200, comprising a single air inlet 604 for air inflow and outflow. The air inlet 604 may be used to control the air pressure within air cavity 402. In some embodiments, air cavity 402 may comprise multiple separate cavities, each comprising an air inlet 604, so that pressure may be applied differentially based on each region of the arm of the subject. In some embodiments, air may be injected into air cavity 402 through air inlet 604 to inflate air cavity 402 and apply pressure on subject 202. In some embodiments, air may be released from air cavity 402 through air inlet 604 to deflate air cavity 402 and release pressure on subject 202. In some embodiments, injection and release of air may be configured to apply constant pressure on subject 202. In some embodiments, injection and release of air may carried out intermittently to apply cyclical pressure on subject 202. Preferably, the pressure applied to subject 202 is cyclical, running at intervals of 50 seconds compression and 10 seconds decompression.

Reference is now made to FIG. 7A which is a schematic illustration of a density of attachment points 304 on liquid cavity 404, and FIG. 7B which is a schematic illustration of a density of attachment points 304 on air cavity 402, in accordance with embodiments of the present disclosure. Attachment points 304 on liquid cavity 404 may be formed between walls 416b and 416c of liquid cavity 404, while attachment points 304 on air cavity 402 may be formed between walls 416a and 416 of air cavity 402. Preferably, attachment points 304 are arranged in a staggered grid format relative to one axis of a grid. Preferably, attachment points 304 have a diameter of between 3 and 10 mm, and ideally 5 mm. In some embodiments, air cavity 402 and liquid cavity 404 may have different densities of attachment points 304. Preferably, liquid cavity 404 may have a high density of attachment points 304 to generate turbulence which would improve liquid flow rates. Preferably, air cavity 402 may have a low density of attachment points 304 as turbulence is not required and the attachment points 304 on air cavity 402 simply serve a structural purpose of preventing ballooning of the air cavity 402. Preferably, the density of attachment points 304 on the air cavity 402 may be between 0.25 and 2 attachment points 304, and preferably 0.5 attachment points 304, per square inch. Preferably, attachment points 304 on the air cavity 402 may have a pitch ratio height of between 15 and 50 mm and ideally 34 mm, and a pitch ratio width of between 20 to 100 mm and ideally 80 mm. Preferably, the density of attachment points 304 on the liquid cavity 404 may be between 3 and 8 attachment points 304, and preferably 5 attachment points 304, per square inch. Preferably, attachment points 304 on the liquid cavity 404 may have a pitch ratio height of between 5 and 40 mm and ideally 10 mm, and a pitch ratio width of between 5 and 40 mm and ideally 20 mm.

Reference is now made to FIG. 8, which is a schematic illustration of first flaps 210 and second flaps 212 of fluid bladder 200 wrapped around a forearm of subject 202, in accordance with embodiments of the present disclosure. The incorporation of multiple flaps (first flaps 210 and second flaps 212) along the fluid bladder 200 allows a one-size-fits-all fluid bladder 200. In addition, if cannulation is required, or if other monitoring devices are required come into contact with the skin of subject 202, while fluid bladder is wrapped around the forearm of subject 202, an operator may undo the flaps at their desired cannulation or monitoring device location to carry out cannulation or attach monitoring device without interfering with the compression process. In some embodiments, cannulation of veins 802 may be carried out by undoing the flaps located above a desired cannulation location to gain access to veins 802. The flaps (first flaps 210 and second flaps 212) may also be undone during limb cooling for intermittent monitoring of the subject with minimal exposure and heat loss or gain during limb cooling.

Figures 9A, 9B, 10A, 10B:
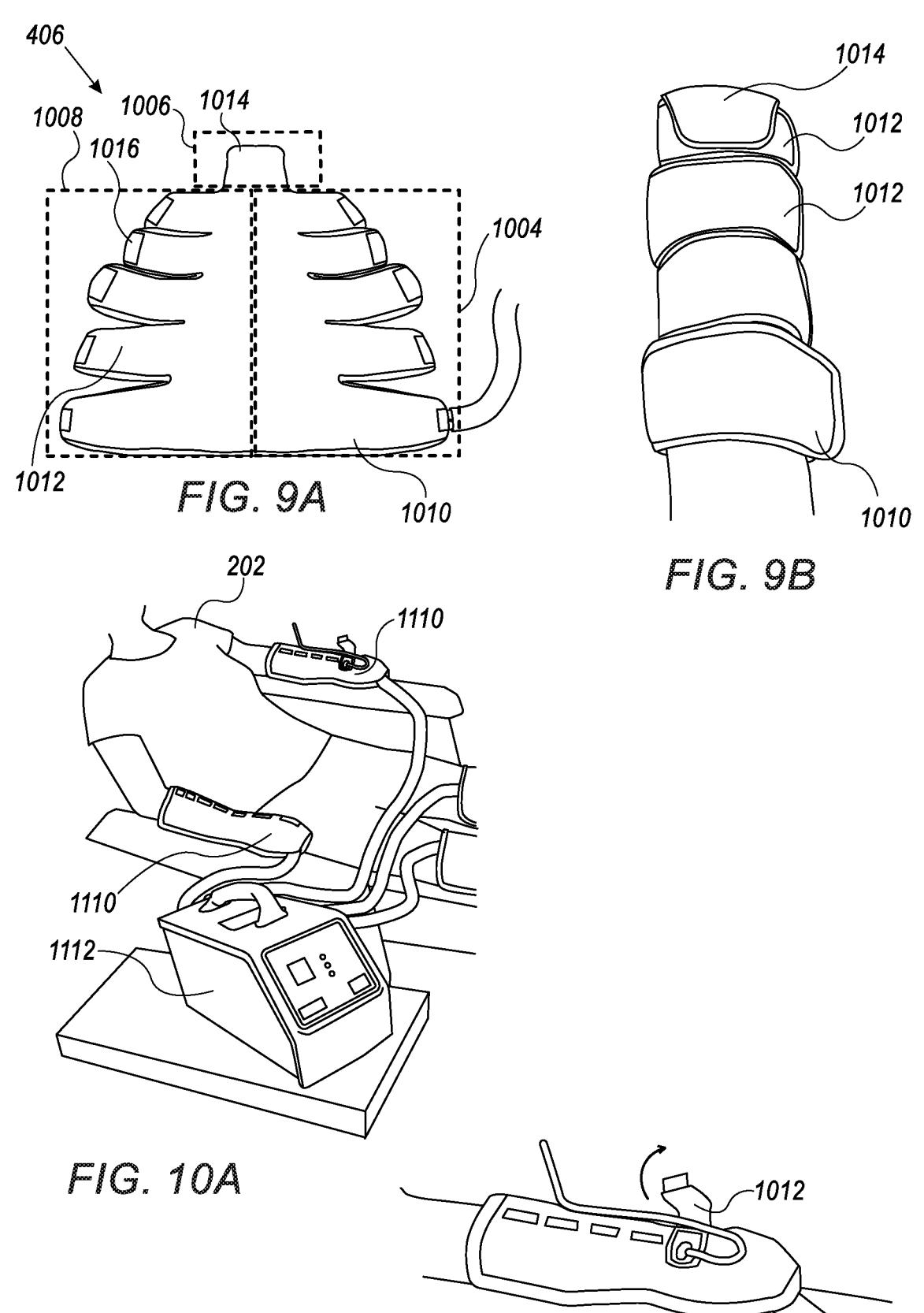
FIG. 9A is a schematic illustration of a sleeve for insertion of a fluid bladder.
FIG. 9B is a schematic illustration of the sleeve after it has been secured around an arm of a subject, in accordance with embodiments of the present disclosure.
FIGS. 10A and 10B are schematic illustrations of a subject with compression wraps secured around both arms, in accordance with embodiments of the present disclosure.

FIG. 9A is a schematic illustration of a sleeve 406 for the insertion of fluid bladder 200, and FIG. 9B is a schematic illustration of a top half of sleeve 406 after it has been secured around the arm of a subject 202, in accordance with embodiments of the present disclosure. Sleeve 406 may be shaped similarly to fluid bladder 200, comprising a first element 1004 with first flaps 1010, a second element 1006 with a digital flap 1014 and a third element 1008 with second flaps 1012. Fluid bladder 200 may be inserted into sleeve 406, with second flaps 212 of fluid bladder 200 inserted into second flaps 1012 of sleeve 406, first flaps 210 of fluid bladder 200 inserted into first flaps 1010 of sleeve 406, and digital flap 214 of fluid bladder 200 inserted into digital flap 1014 of sleeve 406. In some embodiments, each second flap 1012 of sleeve 406 may be wrapped around the arm of subject 202 and secured to their corresponding first flap 1010 of sleeve 406 by any reversible securing mechanism, including a hook and loop material 1016 commonly referred to as Velcro. Digital flap 1014 of sleeve 406 may then be folded and secured to second flap 1012 or first flap 1010 covering the fingers of the subject 202. In other embodiments, digital flap 1014 may be folded over the fingers of a subject 202 before second flap 1012 is folded over digital flap 1014 and secured to the corresponding first flap 1010.

FIGS. 10A and 10B are schematic illustrations of a subject 202 with compression wraps 1110 secured around both arms, in accordance with embodiments of the present disclosure. Cryocompression wrap 1110 may comprise fluid bladder 200 within a sleeve 406. Alternatively, cryocompression wrap 1110 may comprise a fluid bladder 200 fixed between insulating layer 410 and fabric layer 408. In some embodiments, cryocompression wrap 1110 may be connected to a cryocompression apparatus 1112 through liquid inlet 504, liquid outlet 506 and air inlet 604. Cryocompression apparatus 1112 provides coolant to liquid cavity 404 of fluid bladder 200, as well as controls the air pressure in air cavity 402 of fluid bladder 200. In some embodiments, one or more cryocompression wraps 1110 may be connected to and controlled by cryocompression apparatus 1112. Preferably, two cryocompression wraps 1110 are connected and controlled by a cryocompression apparatus 1112. In some embodiments, second flap 1012 located above the dorsal venous or dorsal metacarpal veins may be left open for cannulation and monitoring without exposing too much skin and without interfering with limb cooling on the other regions of the limb of the patient (see FIG. 10B).

Figure 11A:
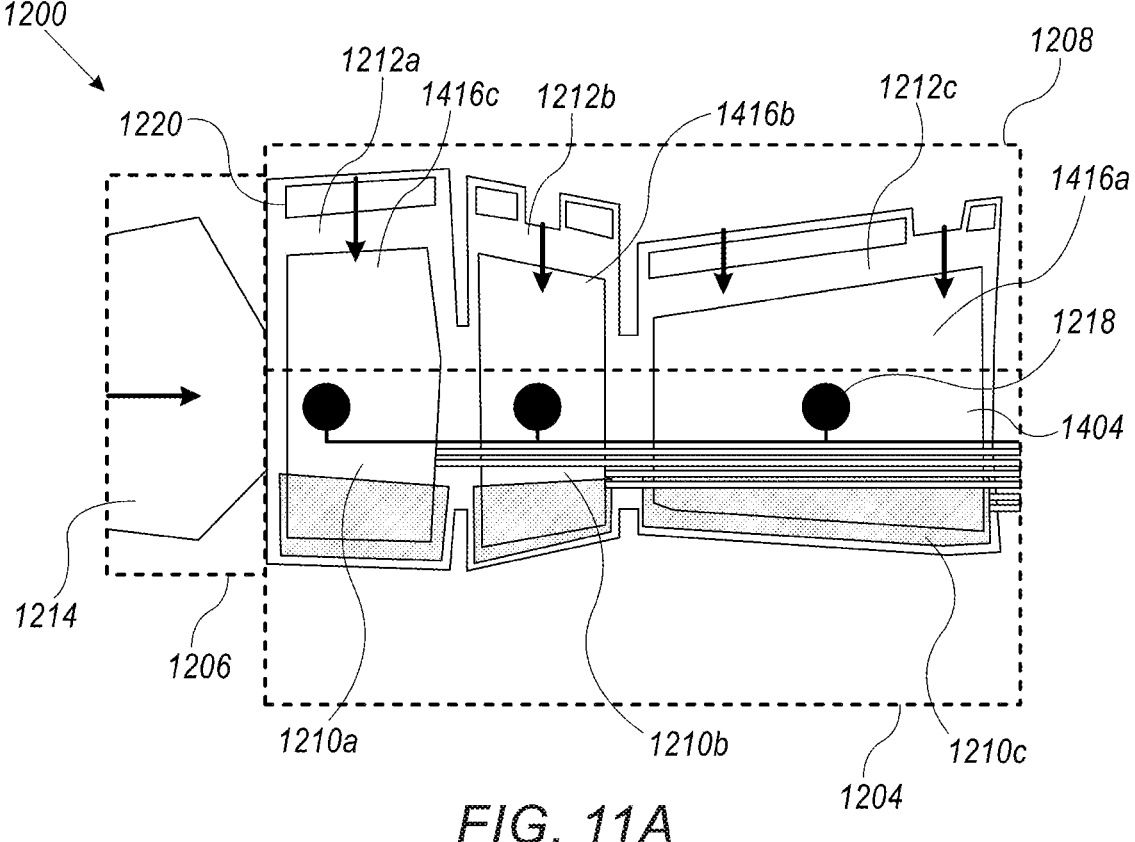
FIGS. 11A and 11B are schematic illustrations of a first alternative compression wrap, in accordance with embodiments of the present disclosure.
Figure 11B:
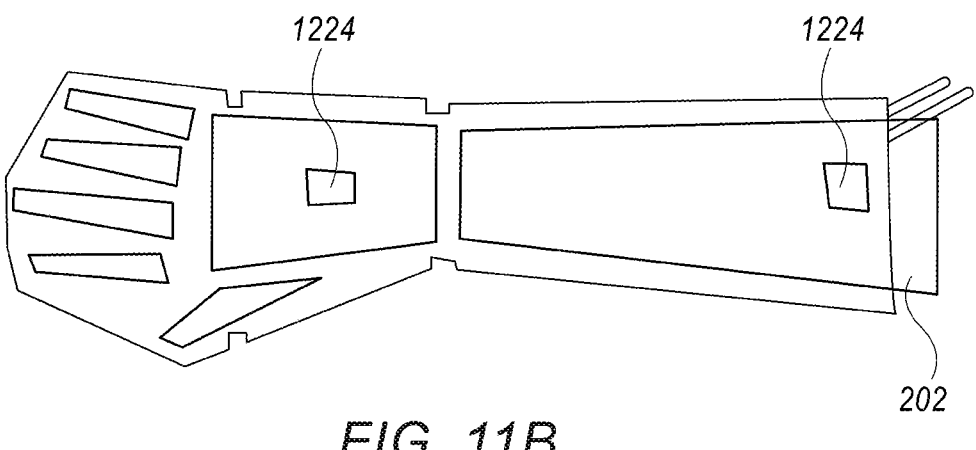

FIGS. 11A and 11B are schematic illustrations of a first alternative compression wrap 1200, in accordance with embodiments of the present disclosure. Similar to fluid bladder 200 and sleeve 406, compression wrap 1200 comprises a first element 1204 for covering at least a first half of the circumference of the arm of a subject 202, a second element 1206 for covering the fingers and a third element 1208 for covering at least a second half of the circumference of the arm of the subject 202, each of the elements 1204, 1206 and 1208 joined to the other two elements. In some embodiments, first element 1204 may comprise three first flaps 1210 spanning the arm of a subject 202: first flap 1210*a* to cover the fingertips, first flap 1210*b* to cover the palm and first flap 1210*c* to cover the forearm. In some embodiments, second element 1206 may comprise a single digital flap 1214 to wrap the fingers. In some embodiments, third element 1208 may comprise three second flaps 1212: second flap 1212*a* to cover the fingertips, second flap 1212*b* to cover the palm and second flap 1212*c* to cover the forearm. In some embodiments, liquid cavity 1404 of compression wrap 1200 may comprise three or more liquid packets 1416 to receive coolant. In some embodiments, liquid cavity 1404 of may comprise a first liquid packet 1416*a* to cover a forearm region, a second liquid packet 1416*b* to cover a palm region, and a third liquid packet 1416*c* to cover a finger region. In some embodiments, the three or more liquid packets 1416 may be fluidly separate from each other, with individual coolant inlets and outlets tubes connected to each liquid packet 1416.

According to some embodiments of the present disclosure, first alternative compression wrap 1200 may further comprise one or more temperature sensors 1218 to monitor a temperature of the skin of the subject 202 during limb hypothermia. The first flaps 1210 and second flaps 1212 may be secured together with hoop and loop material 1220 commonly referred to as Velcro. In some embodiments, first flaps 1210 and second flaps 1212 may include openings 1224 for observation and/or cannulation when compression wrap 1200 is secured around the arm of a subject 202, as illustrated in FIG. 11B.

Figure 12:
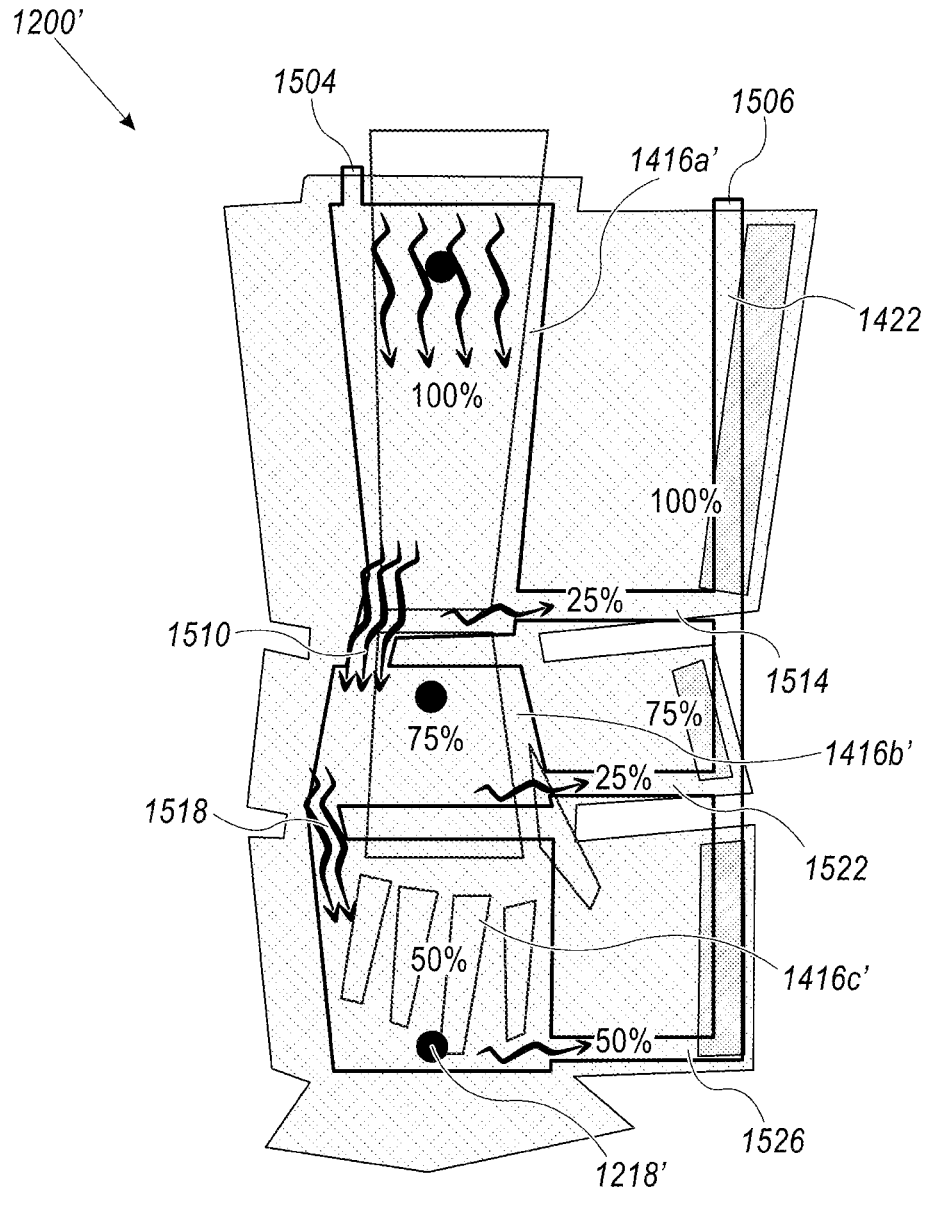
FIG. 12 is a schematic illustration of a second alternative compression wrap, in accordance with embodiments of the present disclosure.

FIG. 12 is a schematic illustration of a second alternative compression wrap 1200', in accordance with embodiments of the present disclosure. The second alternative compression wrap 1200' is similar to first alternative compression wrap 1200 except that the three or more liquid packets 1416' are fluidly connected. In some embodiments, the three or more liquid packets 1416' may be fluidly connected to each other using a bottleneck design to reduce flow and adjust temperature incrementally through different zones configured to cover different regions of the arm of subject 202. Coolant may first be introduced through liquid inlet 1504 into a first liquid packet 1416*a*' covering the forearm region. The coolant may then be divided into two streams: a first stream 1510 flowing into a second liquid packet 1416*b*' covering the palm region, and a second stream 1514 flowing into an outlet tube 1222 and out of compression wrap 1200' through liquid outlet 1506. In some embodiments, about 75% of the total coolant volume introduced into liquid hypothermia wrap 1200 may flow through first stream 1510 into second liquid packet 1416*b*' covering the palm area, with the remaining 25% flowing into outlet tube 1222 through liquid outlet 1506 out of compression wrap 1200'.

According to some embodiments of the present disclosure, the coolant that flowed into the liquid packet 1416*b*' covering the palm area may then be further divided into two streams: a third stream 1518 flowing into a third liquid packet 1416*c*' covering the finger area, and a fourth stream 1522 flowing into outlet tube 1222 out of the compression wrap 1200' through liquid outlet 1506. In some exemplary embodiments, about 50% of the total coolant volume introduced into liquid hypothermia wrap 1200' flows into third liquid packet 1416*c*' covering the finger area. In some embodiments, all the coolant that entered into third liquid packet 1416*c*' covering the finger area may then flow through a fifth stream 1526 into outlet tube 1222 out of the compression wrap 1200' through liquid outlet 1506. This significantly reduces the number of inlet and outlet tubes connected to second alternative compression wrap 1200' as compared to first alternative compression wrap 1200. In some other alternative embodiments, the total coolant volume introduced into second liquid packet 1416*b* and third liquid packet 1416*c* may be further reduced to about 40% and about 20% respectively. In yet other alternative embodiments, the total coolant volume introduced into second liquid packet 1416*b* and third liquid packet 1416*c* may be further reduced to about 30% and about 10% respectively.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A compression wrap for temperature-controlled application of pressure on an arm of a subject, the compression wrap comprising:

a fluid bladder comprising:

a first element comprising two or more first flaps;

a second element comprising one or more digital flaps;

a third element comprising two or more second flaps, wherein the first element and the third element are connected along a first edge and the second element is connected to the first element and the third element along a second edge;

a fluid cavity configured to be deposed proximate to the arm; and an air cavity configured to compress the fluid cavity against the arm;

wherein the liquid cavity comprises a liquid inlet and a liquid outlet, the liquid inlet disposed on a first flap or a second flap and away from the second element, the liquid cavity comprising a passageway that runs through the liquid cavity from the liquid inlet to the liquid outlet.

2. The compression wrap of claim 1, wherein the first element of the fluid bladder is configured to cover at least a first half of a circumference of the arm of a subject and the third element of the fluid bladder is configured to cover at least a second half of the circumference of the arm of a subject.

3. The compression wrap of claim 1, wherein each of the two or more second flaps corresponds to one of the two or more first flaps.

4. The compression wrap of claim 1, wherein each of the two or more second flaps is removably attached to a corresponding first flap.

5. The compression wrap of claim 1, wherein the two or more first flaps and the two or more second flaps extend perpendicularly from the first edge.

6. The compression wrap of claim 1, wherein the two or more first flaps are separated from each other with slits terminating within the first element.

7. The compression wrap of claim 1, wherein the two or more second flaps are separated from each other with slits terminating within the third element.

8. The compression wrap of claim 1, wherein the air cavity comprises between 0.25 and 2 attachment points per square inch.

9. The compression wrap of claim 1, wherein the air cavity comprises attachment points with a pitch ratio height of between 15 and 50 mm and a pitch ratio width of between 20 to 100 mm.

10. The compression wrap of claim 1, wherein the passageway runs along a perimeter of each of the two or more first flaps, the one or more digital flaps, and two or more second flaps.

11. The compression wrap of claim 1, wherein the liquid cavity comprises between 3 and 8 attachment points per square inch.

12. The compression wrap of claim 1, wherein the liquid cavity comprises attachment points with a pitch ratio height of between 5 and 40 mm and a pitch ratio width of between 5 and 40 mm.

13. The compression wrap of claim 1, wherein the liquid cavity comprises three or more liquid pockets.

14. The compression wrap of claim 1, further comprising a fabric layer positioned against the liquid cavity and an insulating layer positioned against the air cavity.

15. A method of applying temperature-controlled pressure to an arm of a subject, the method comprising:

providing a compression wrap, the compression wrap comprising:

a fluid bladder comprising:

a first element comprising two or more first flaps;

a second element comprising one or more digital flaps; and a third element comprising two or more second flaps, wherein the first element and the third element are connected along a first edge and the second element is connected to the first element and third element along a second edge;

securing the compression wrap on the arm by attaching each of the two or more second flaps to a corresponding first flap; and injecting air and coolant into the fluid bladder;

whereincoolant is injected into a liquid cavity of the fluid batter, the liquid cavity positioned against the subject, thenliquid cavity comprising a liquid inlet and a liquid outlet, the liquid inlet disposed on a first flap or second flap and away from the second element, the liquid cavity comprising a passageway that runs through the liquid cavity from the liquid inlet to the liquid outlet.

16. The method of claim 15, wherein air is injected into an air cavity of the fluid bladder, the air cavity positioned above the liquid cavity.

17. The method of claim 16, wherein air is injected into and released from the air cavity intermittently to provide cyclical pressure on the subject.

18. The method of claim 15, further comprising detaching and reattaching one of the two or more second flaps from the corresponding first flap to monitor the subject.

\* \* \* \* \*